(12) United States Patent
Fuerst et al.

(10) Patent No.: US 11,261,473 B2
(45) Date of Patent: Mar. 1, 2022

(54) METHOD AND APPARATUS FOR GENERATION OF MICROPARTICLES CONTAINING IMMOBILIZED ENZYME

(71) Applicant: Roche Diabetes Care, Inc., Indianapolis, IN (US)

(72) Inventors: Otto Fuerst, Viernheim (DE); Herbert Harttig, Neustadt (DE); Bernd Hiller, Lampertheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 69 days.

(21) Appl. No.: 15/326,519

(22) PCT Filed: Jul. 23, 2015

(86) PCT No.: PCT/EP2015/066936
§ 371 (c)(1),
(2) Date: Jan. 16, 2017

(87) PCT Pub. No.: WO2016/012564
PCT Pub. Date: Jan. 28, 2016

(65) Prior Publication Data
US 2017/0226500 A1   Aug. 10, 2017

(30) Foreign Application Priority Data
Jul. 23, 2014 (EP) .................................... 14178121

(51) Int. Cl.
| | | |
|---|---|---|
| *C12Q 1/00* | (2006.01) | |
| *G01N 33/66* | (2006.01) | |
| *A61K 9/50* | (2006.01) | |
| *C12N 11/04* | (2006.01) | |
| *C12N 9/04* | (2006.01) | |
| *C12N 11/10* | (2006.01) | |
| *C12Q 1/54* | (2006.01) | |
| *B05B 7/16* | (2006.01) | |

(52) U.S. Cl.
CPC ............ *C12Q 1/006* (2013.01); *A61K 9/5089* (2013.01); *C12N 9/0006* (2013.01); *C12N 11/04* (2013.01); *C12N 11/10* (2013.01); *C12Q 1/54* (2013.01); *C12Y 101/01047* (2013.01); *C12Y 101/03004* (2013.01); *G01N 33/66* (2013.01); *A61K 9/5036* (2013.01); *B05B 7/1686* (2013.01)

(58) Field of Classification Search
CPC ...... C12N 11/10; C12N 9/0006; C12N 11/04; C12Y 101/03004; C12Y 101/01047; C12Q 1/54; C12Q 1/006; G01N 33/66; A61K 9/5089; A61K 9/5036; B05B 7/1686
See application file for complete search history.

(56) References Cited

U.S. PATENT DOCUMENTS

| | | | | |
|---|---|---|---|---|
| 4,004,733 A | * | 1/1977 | Law | B05B 5/043 239/3 |
| 4,443,538 A | * | 4/1984 | Cheetham | C12N 11/04 435/170 |
| 5,286,495 A | * | 2/1994 | Batich | A61K 9/1652 424/488 |
| 5,429,821 A | * | 7/1995 | Dorian | A01N 1/02 264/4.1 |
| 6,274,174 B1 | * | 8/2001 | Hom-ma | A61K 9/146 424/469 |
| 2004/0009230 A1 | * | 1/2004 | Richard | B01D 33/11 424/489 |
| 2004/0265811 A1 | * | 12/2004 | Reardon | C12Q 1/002 435/6.11 |
| 2007/0178162 A1 | * | 8/2007 | Kammermeier | A61K 9/5036 424/489 |
| 2010/0035245 A1 | | 2/2010 | Stiene et al. | |
| 2010/0233115 A1 | * | 9/2010 | Patel | A61L 15/26 424/78.08 |

(Continued)

FOREIGN PATENT DOCUMENTS

| | | |
|---|---|---|
| EP | 0 162 302 A1 | 11/1985 |
| WO | WO 2016/012564 A1 | 1/2016 |

OTHER PUBLICATIONS

Zhang, J et al. Theoretical and experimental investigations on the size of alginate microspheres prepared by dropping and spraying. 2007. Journal of Microencapsulation. 24(4): 303-322. (Year: 2007).*

Kwok, KK et al. Production of 5-15 microns diameter alginate-polylysine microcapsules by an air-atomization technique. Pharmaceutical Research. 1991. 8(3): 341-344. (Year: 1991).*

Kim, SG et al. Preparation of sodium alginate hydrogel microparticles by electrospinning using various types of salts. Polymers & Polymer Composites. 2010. 18(7): 397-404. (Year: 2010).*

(Continued)

*Primary Examiner* — Renee Claytor
*Assistant Examiner* — Susan E. Fernandez
(74) *Attorney, Agent, or Firm* — Woodard, Emhardt, Henry, Reeves & Wagner, LLP

(57) ABSTRACT

A method and an apparatus are described for the generation of microparticles containing an immobilized functional component, where the following measures are proposed:
spraying a liquid (32) containing a soluble alginate and a functional component consisting of molecules or nanoparticles to generate a stream (60) of droplets,
directing the stream (60) of droplets onto a precipitation bath (16) and capturing the droplets therein by application of high voltage (14),
precipitating the droplets in the precipitation bath (16) via a precipitation liquid (18) containing an alginate complexing agent, such that the droplets are solidified to form microparticles (10) containing the functional component and
extracting the microparticles (10) from the precipitation bath (16).

25 Claims, 1 Drawing Sheet

(56) References Cited

U.S. PATENT DOCUMENTS

Figure 1:
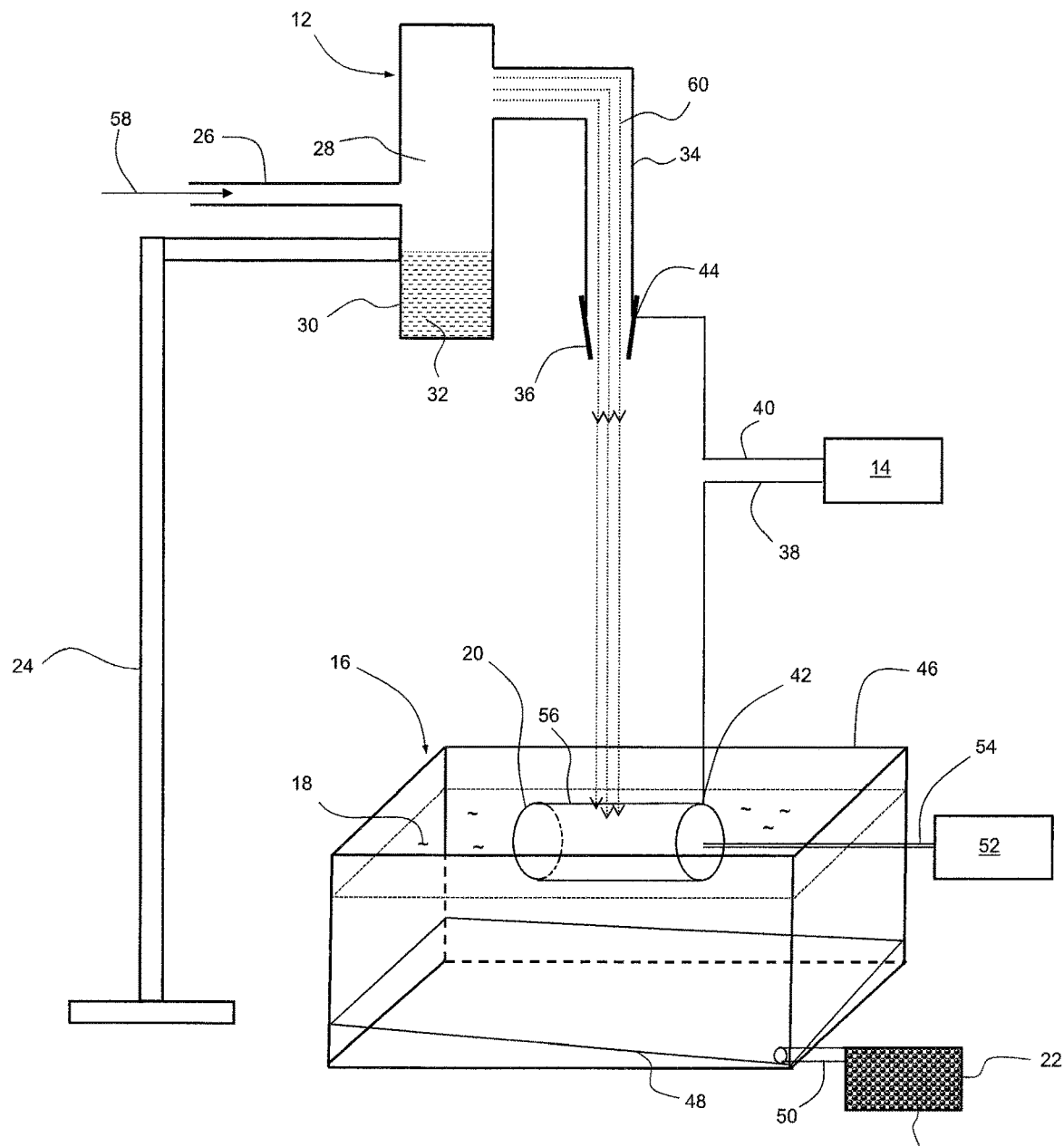

2011/0008293 A1* 1/2011 Bhandari .............. A01N 25/28
                                                        424/93.6
2012/0270295 A1* 10/2012 Choo ................ G01N 33/5005
                                                        435/178

OTHER PUBLICATIONS

Morch, YA et al. Effect of Ca2+, Ba2+, and Sr2+ on alginate microbeads. Biomacromolecules. 2006. 7: 1471-1480. (Year: 2006).*
Wang, W et al. Investigation on the correlations between droplet and particle size distribution in ultrasonic spray pyrolysis. Ind. Eng. Chem. Res. 2008. 47: 1650-1659. (Year: 2008).*
European Patent Application No. 15741210.7 Office Action dated Oct. 5, 2018. 7 pages.
Herrero, E.P. et al., "Development of a new technology for the production of microcapsules based in atomization processes". Chemical Engineering Journal, vol. 117, No. 2, Apr. 2006, pp. 137-142. 6 pages.
Huang, Keng-Shiang et al., "Electrostatic droplets assisted synthesis of alginate microcapsules," Drug Delivery and Translation Research, vol. 1, No. 4, Mar. 22, 2011. 10 pages.
International Patent Application PCT/EP20115/066936 International Search Report and Written Opinion dated Sep. 25, 2015. 11 pages.
Watanabe, Hideo et al., "Preparation of immobilized enzyme gel particles using an electrostatic atomization technique," Biochemical Engineering Journal, vol. 8, No. 2, Sep. 1, 2001. 4 pages.

* cited by examiner

METHOD AND APPARATUS FOR GENERATION OF MICROPARTICLES CONTAINING IMMOBILIZED ENZYME

The invention concerns a method and an apparatus for generation of microparticles containing an immobilized functional component, specifically an enzyme or other functional molecules or sub-micro-sized particles (nanoparticles). The invention further concerns a diagnostic test element, specifically glucose test element.

In diagnostic test elements or sensors for glucose tests it is known to provide enzymes in a reagent layer or electrode layer to induce chemical reactions which are responsive to an analyte in a body fluid contacted with the test element. Such analyses are usually made with handheld devices on the spot by patients themselves. There, it should be guaranteed that the enzymes are immobilized without skin contact, and that the enzymes can be reached by diffusion of the sample ingredients in a given measurement time. In this context, it is known to include the enzymes in a wet chemistry composition which is applied on a substrate and further coated after drying.

On this basis the object of the invention is to further improve the known methods and for generation of microparticles and to provide improved diagnostic test elements specifically for self-testing glucose measurement systems.

The combination of features stated in the independent claims is proposed to achieve this object. Advantageous embodiments and further developments of the invention are derived from the dependent claims.

The invention is based on the idea of generating solidified microparticles as a carrier for at least one immobilized functional component, which has a specific function in a diagnostic test. Accordingly it is proposed according to the invention that a method for generation of microparticles comprises the steps of a) spraying a liquid which contains a soluble alginate and a functional component consisting of molecules or nanoparticles to generate a stream of droplets, wherein spraying the liquid comprises applying a gas stream to the liquid, thereby atomizing the liquid in the gas stream, b) directing the stream of droplets onto a precipitation bath and capturing the droplets therein by application of high voltage, c) precipitating the droplets in the precipitation bath by means of a precipitation liquid containing an alginate complexing agent, whereby the droplets are solidified to form microparticles containing the functional component, and d) extracting the microparticles from the precipitation bath.

In such a way, it is possible to create particles from a physiological non-hazardous material and of very small size, i.e. at most 100 microns, so that there is provided a comparatively large surface for the analytes to reach the functional component which is immobilized in the particles structure. An adequate particle size can be achieved by atomizing a liquid and by directing a mist-like stream of droplets under the influence of a high voltage to a precipitation bath, such that a considerable yield is achieved and the spray is not lost before reaching the precipitation liquid. By atomizing the liquid in the gas stream, there is no need for a complex electrostatic atomization technique. Moreover, such a gas stream allows adjustment of the droplet size by simple measures such as adjusting the velocity and temperature of the carrier gas. Thus, the generation of a stream of droplets in a gas stream provides further degrees of freedom: The droplet size can be adjusted independent of the voltage of a potential subsequent electrostatic charge. By means of increasing the gas pressure, it is possible to decrease the average diameter of the droplets, even below a dimension which is achievable by electrostatic atomization of a given liquid, e.g. to 2-10 μm. The droplet dimension is not influenced, neither by the distance to the precipitation bath nor by the electric conductivity of the initial solution nor by the magnitude of an applied high voltage. Furthermore, it is possible to achieve a high throughput with simple measures.

According to a preferred embodiment, the molecules forming the functional component are selected from the group of enzymes, coenzymes, mediators, stabilizers and dyes, and preferably are enzymes.

It is also preferred that the nanoparticles forming the functional component are sized in at least one dimension, preferably in 3 dimensions, below 1 μm. The nanoparticles may preferably be selected from the group of metal, metal alloy, metal oxide and carbon.

Advantageously also with respect to a simplified arrangement, spraying the liquid in the afore-mentioned step a) comprises applying a gas stream to the liquid provided in a reservoir.

For further improvement of the yield of generated particles, it is advantageous when a moving surface is provided in the precipitation bath, wherein the moving surface is continuously loaded with a film of the precipitation liquid and the droplets are disposed onto the moving surface such that agglutination of droplets or particles is avoided.

Another improvement provides that a target electrode connected to the high voltage is arranged in the precipitation bath, specifically in the form of a submerged rotating drum. This allows to provide a focused attractive force in addition to gravitation.

For further production improvement it is advantageous when an electrically conductive nozzle is connected as an electrode to the high voltage, and the stream of previously generated droplets is directed through the nozzle.

Surprisingly, the electrostatic charging of the droplets within the gas stream during passage of the high voltage nozzle works without problems and efficiently. Without the need for a direct contact with the nozzle, an electrostatic charging of the droplets occurs, which is used to bring the droplets in effective contact with the precipitation bath. Due to the electric charge, an attractive force occurs in direction to the inversely poled precipitation bath, which brings the micro-droplets in contact with the bath surface.

In a particular embodiment the microparticles are formed with a dimension of less than 50 μm, e.g. in the range from 1 to 20 μm, preferably less than 20 μm, e.g. in the range from 1 to 10 μm, and more preferably less than 10 μm, e.g. in the range from 0.1 to 5 μm. Microparticles of such a small size provide sufficient surface as a diffusion interface, and with a limited size distribution preferably in the single-digit micron range it is possible to achieve a homogenous response.

Advantageously, the method further comprises the step of separating microparticles of different size by an ion exchange process using different ions in the alginate complexing agent, specifically barium ions and calcium ions.

For further improvement of the practical value it is advantageous when the microparticles are provided with a stabilizing shell made of a polymer material, specifically of polycations.

An intermediate product can be generated for further processing by discharging a suspension of the microparticles through an outlet of the precipitation bath.

It is also favorable when the microparticles are treated in a cleaning bath by means of an ion exchange process, specifically to remove biological hazardous substances.

In regard to a preferred use it is advantageous when the microparticles are deposited in a layer of a diagnostic test element, specifically in a reagent layer or electrode layer of a glucose test element.

With regard to an apparatus adapted for generation of microparticles containing an immobilized functional component, in order to solve the aforementioned object, it is proposed to provide a modular arrangement comprising the following components:

- a spraying unit adapted to generate a stream of droplets of a liquid containing a soluble alginate and the functional component, wherein the stream of droplets is generated by applying a gas stream to the liquid, thereby atomizing the liquid in the gas stream,
- a high voltage unit adapted for charging and directing the droplets to a target electrode and
- a precipitation bath containing the target electrode and an alginate complexing agent adapted to precipitate the droplets, such that the droplets are solidified to form microparticles,
- means adapted to extract the microparticles from the precipitation bath.

A further improvement comprises an electrically conductive nozzle which is connected as an electrode to the high voltage unit, wherein the stream of previously generated droplets is directed through the nozzle in order to charge the droplets.

Another aspect of the invention concerns a diagnostic test element, specifically glucose test element, comprising a reagent layer or electrode layer, wherein said layer comprises microparticles containing at least one immobilized functional component which consists of molecules or nanoparticles.

The proposed inclusion of microparticles is particularly effective when a two-layer structure comprising an intermediate and an outer layer is applied on a carrier substrate, and when the microparticles are included in the intermediate layer.

Advantageously, the molecules forming the functional component are selected from the group of enzymes, coenzymes, mediators, stabilizers, and dyes.

Further advantageously and specifically tailor-made for blood glucose tests, the at least one functional component is an enzyme which is selected from the following group of enzymes: oxi-reductase-enzymes, e.g. GlucDOR/PQQ (Glucose Dye Oxidoreductase), dehydrogenase-enzymes, e.g. glucose dehydrogenase, in particular NAD-dependent glucose dehydrogenase, FAD-dependent glucose dehydrogenase and/or PQQ-dependent glucose dehydrogenase, oxidase-enzymes, e.g. glucose oxidase.

Generally, the sub-micro-sized particles or nanoparticles forming the functional component are considerably smaller than the microparticles and have a diameter of less than 1 μm, preferably 1 to 500 nm, especially preferred of 1 to 100 nm.

The material of the nanoparticles usually is one of metal and metal alloy and metal oxide and carbon.

When acting as a catalyst, the nanoparticles are selected of at least one of platinum and palladium and silver and rhenium and rhodium and iron and nickel and cobalt and copper and chromium and zinc and aluminium and manganese and molybdenum or alloys thereof or oxides thereof.

Alternatively, the nanoparticles are quantum dots acting as a fluorescent dye.

As a further alternative, the nanoparticles are an electric conductor selected out of metals, metal oxides or carbon, e.g. in the form of nanowires or nanotubes acting as a contributor to the electric conductivity of the reagent layer.

The invention is further elucidated in the following on the basis of an embodiment example shown schematically in the drawings, where FIG. 1 is a schematic view of an apparatus for generation of microparticles;

FIG. 2 is sectional view of a layered diagnostic test element comprising microparticles.

FIG. 1 illustrates a system or apparatus for generation of microparticles 10 comprising a spraying unit 12, a high voltage unit 14, a precipitation bath 16 including a precipitation liquid 18 and a rotatable drum 20, and extraction means 22 for extracting precipitated microparticles 10 from the bath 16.

The spraying unit 12, which can be positioned over the precipitation bath 16 by means of a stand 24, is provided with a gas inlet 26, an atomizer chamber 28 including a reservoir 30 for a feed liquid 32 and an aerosol outlet 34 ending in a discharge nozzle 36. The feed liquid 32 contains an aqueous solution of a soluble alginate, e.g. sodium alginate and at least one of enzyme selected from oxireductase-enzymes, dehydrogenase-enzymes or oxidase-enzymes and other functional molecules. Therewith, it is finally aimed to form beads of alginate complexes containing immobilized enzymes as (spherical) microparticles with a size or dimension (diameter) in the range from 1 to 20 μm.

The high voltage unit 14 has a source 38 for a d.c. voltage in the range of 3 to 80 kV, preferred 10 to 60 kV which is supplied between a first port 38 and a second port 40. First port 38, suitably grounded, is connected to the drum 20 which thereby forms a target electrode 42, whereas second port 40 is connected to the nozzle 36 forming a counter electrode 44. Optionally, the first port 38 may be connected to the precipitation liquid 18, and second port 40 may be connected to charge the feed liquid 32.

The precipitation bath 16 comprises an open-top container 46 which has an inclined bottom plane 48 for guiding precipitated microparticles 10 to a discharge connection 50 of the extraction means 22.

The horizontally oriented drum 20 is rotatable around its center axis by means of a motor 52, where the output shaft 54 is arranged along the fluid level of the precipitation liquid 18. In this way, the cylindrical mantle of the rotated drum 20 is partially submersed and hence forms a moving surface 56 which is continuously loaded with a revolving film of the precipitation liquid 18.

The system may comprise a central control unit (not shown) for controlling the operating procedure and the process parameters of the various system units.

In use, the inlet 26 of the spraying unit 12 is loaded with a stream 58 of a carrier gas, e.g. air provided from a compressor. Under the effect of the gas stream 58, the feed liquid 32 is atomized into nebular droplets. Advantageously, the size of the droplets is adjusted by the velocity, temperature and humidity of the carrier gas, wherein evaporation leads to a miniaturization of the droplets during flight. In this stage, a fine aerosol jet 60 is generated by non-electric effects.

Then, the jet 60 is ejected through the nozzle 36, where the droplets are electrically charged to a high potential. The nozzle 36 directs the jet 60 against the drum 20, where the charged droplets are attracted by the target electrode 42 and captured in the film of the precipitation liquid 18 coating the mantle or moving surface 56.

The precipitation liquid 18 contains an aqueous solution of an alginate complexing agent including e.g. $Ba^{2+}$ ions which permeate the droplets and lead to solidified beads or microparticles 10 containing immobilized enzyme(s).

In addition to the complexing agent, further ingredients may be provided in the precipitation liquid 18 to structurally stabilize the developing beads on their surface. This may be achieved by polymers, specifically polycations, which preferentially adsorb on the surface of the beads and form a complex with the solidifying alginate component thereby providing a stabilizing outer shell.

The solidified beads which sediment on the inclined bottom plane 48 are guided to the discharge connection 50, where a suspension of microparticles 10 can be discharged to the extraction means 22 either in a continuous or a batch mode.

It is also conceivable to separate microparticles of different size by a cation ion exchange process. When the microparticles 10, which were precipitated with ions of comparatively high atomic mass, are fed into a solution of a precipitating ion of lower atomic mass, e.g. $Ca^{2+}$ in a saturated $CaSO_4$-solution, an ion exchange process occurs with the resulting beads having a lower density. As this happens faster on smaller particles having a comparatively larger surface, smaller beads will ascend in the solution, and a separation can be achieved by decantation. At the same time, the ion exchange process leads to a cleaning in the sense of a reduced toxicity of $Ca^{2+}$-containing microparticles 10.

The microparticles 10 containing immobilized enzyme(s) are particularly useful in diagnostic test elements designed for glucose tests. Such test elements may be provided on disposable test tapes or test strips, either for optical or electrochemical analyses.

Figure 2:
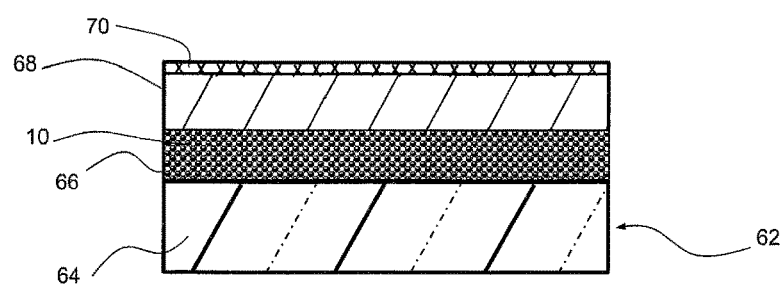

FIG. 2 shows a sectional view of a glucose test element 62 which is generally designed as a two-layered composite on a substrate 62 formed by a transparent plastic carrier. The substrate 62 is coated with a first layer 66 of a reactive test material. This material contains microparticles 10 including immobilized enzymes and some of functional molecules as mediator and dye. The latter reacts by a color change induced by the enzymes which are responsive to glucose. In one exemplary composition, oxidase- or dehydrogenase enzymes are used, e.g. glucose oxidase or glucose dehydrogenase, and the dye includes molybdenum in the form of phosphomolybdic acid.

The first layer 66 is covered by a second layer 68 of test material containing most of the mediator and of the dye which are also present in the first layer. Further, the second layer 68 contains white pigments for separation of a blood sample and for providing a white background for optical measurement of the color change. It is notably important to avoid that enzymes and other functional molecules permeate the optical barrier formed by the second layer 68 specifically during drying of the respective wet chemistry composition. The microparticles 10 immobilize the enzymes in such a way that they cannot reach the second layer 68 during the manufacturing or analysis process.

On the upper side of the test element 62, a spreading web 70 is attached for homogenous and planar distribution of a blood sample. When conducting a diagnostic test, the blood sample is applied by the user as a droplet from a skin wound.

The invention claimed is:

1. A method for generation of microparticles containing an immobilized functional component, the method comprising the steps of a) spraying a liquid which contains a soluble alginate and a functional component consisting of molecules or nanoparticles to generate a stream of droplets, wherein spraying the liquid comprises applying a gas stream to the liquid, thereby atomizing the liquid in the gas stream, wherein said spraying the liquid comprises
      providing the liquid as a static volume in a reservoir,
      applying the gas stream to the liquid in the reservoir, and
      adjusting size of the droplets by adjusting a property of the gas stream,
   b) directing the stream of the previously generated droplets through an electrically conductive nozzle which is connected as a counter electrode to a high voltage, wherein the high voltage is in a range of 3 to 80 kV,
   c) directing the stream of the droplets onto a precipitation bath and capturing the droplets therein by application of the high voltage, wherein a target electrode connected to the high voltage is positioned within the precipitation bath,
   d) precipitating the droplets in the precipitation bath by means of a precipitation liquid containing an alginate complexing agent, such that the droplets are solidified to form microparticles containing the functional component, and
   e) extracting the microparticles from the precipitation bath.

2. The method of claim 1, wherein the molecules forming the functional component are selected from the group of enzymes, coenzymes, mediators, stabilizers and dyes, and/or wherein the nanoparticles forming the functional component are sized in at least one dimension below 1 μm and/or are selected from the group of metal, metal alloy, metal oxide and carbon.

3. The method of claim 2, wherein the molecules forming the functional component are enzymes.

4. The method according to claim 1, further comprising providing a moving surface in the precipitation bath, wherein the moving surface is continuously loaded with a film of the precipitation liquid and the droplets are disposed onto the moving surface.

5. The method according to claim 1, wherein the target electrode is in the form of a submerged rotating drum.

6. The method according to claim 1, wherein the microparticles are formed with a dimension of less than 50 μm.

7. The method according to claim 6, wherein the microparticles are formed with a dimension in the range from 1 to 20 μm.

8. The method according to claim 1, further comprising separating microparticles of different size by an ion exchange process using different ions in the alginate complexing agent, wherein the ions are barium ions and calcium ions.

9. The method according to claim 1, further comprising providing the microparticles with a stabilizing shell made of a polymer material.

10. The method according to claim 1, further comprising discharging a suspension of the microparticles through an outlet of the precipitation bath.

11. The method according to claim 1, further comprising cleaning of the microparticles in a cleaning bath by means of an ion exchange process.

12. The method according to claim 1, further comprising depositing the microparticles in a layer of a diagnostic test element, wherein the layer is selected from a reagent layer or an electrode layer and the diagnostic test element is a glucose test element.

13. The method of claim 1, wherein the property of the gas stream includes at least one of velocity, temperature, and humidity of the gas stream.

14. A method for generation of microparticles containing an immobilized functional component, the method comprising the steps of:
  a) spraying a liquid which contains a soluble alginate and a functional component consisting of molecules or nanoparticles to generate a stream of droplets, wherein spraying the liquid comprises applying a gas stream to the liquid, thereby atomizing the liquid in the gas stream, wherein said spraying includes adjusting size of the droplets by adjusting at least one of velocity, temperature, and humidity of the gas stream,
  b) directing the stream of droplets onto a precipitation bath and capturing the droplets therein by application of high voltage, wherein an electrically conductive nozzle is connected as a counter electrode to the high voltage, wherein said directing the stream includes
    electrostatically charging the droplets by directing the stream of the droplets through the nozzle, wherein the droplets are generated before being electrostatically charged by the nozzle,
    wherein the high voltage to electrostatically charge the previously generated droplets with the nozzle is in a range of 3 to 80 kV, and
    wherein a target electrode connected to the high voltage is positioned within the precipitation bath,
  c) precipitating the droplets in the precipitation bath by means of a precipitation liquid containing an alginate complexing agent, such that the droplets are solidified to form microparticles containing the functional component, and
  d) extracting the microparticles from the precipitation bath.

15. The method of claim 14, wherein the molecules forming the functional component are selected from the group of enzymes, coenzymes, mediators, stabilizers and dyes, and/or wherein the nanoparticles forming the functional component are sized in at least one dimension below 1 μm and/or are selected from the group of metal, metal alloy, metal oxide and carbon.

16. The method of claim 15, wherein the molecules forming the functional component are enzymes.

17. The method according to claim 14, further comprising providing a moving surface in the precipitation bath, wherein the moving surface is continuously loaded with a film of the precipitation liquid and the droplets are disposed onto the moving surface.

18. The method according to claim 14, wherein the target electrode is in the form of a submerged rotating drum.

19. The method according to claim 14, wherein the microparticles are formed with a dimension of less than 50 μm.

20. The method according to claim 19, wherein the microparticles are formed with a dimension in the range from 1 to 20 μm.

21. The method according to claim 14, further comprising separating microparticles of different size by an ion exchange process using different ions in the alginate complexing agent, wherein the ions are barium ions and calcium ions.

22. The method according to claim 14, further comprising providing the microparticles with a stabilizing shell made of a polymer material.

23. The method according to claim 14, further comprising discharging a suspension of the microparticles through an outlet of the precipitation bath.

24. The method according to claim 14, further comprising cleaning of the microparticles in a cleaning bath by means of an ion exchange process.

25. The method according to claim 14, further comprising depositing the microparticles in a layer of a diagnostic test element, wherein the layer is selected from a reagent layer or an electrode layer and the diagnostic test element is a glucose test element.

* * * * *